United States Patent [19]

Blombäck et al.

[11] 4,229,435
[45] Oct. 21, 1980

[54] PREPARATION OF BLOOD FRACTION

[76] Inventors: Birger E. G. Blombäck, 31 Tomtebogatan S-113 38, Stockholm; Dagny B. Hessel, 139 Rädisvagen, S-162 41 Vällingby, both of Sweden

[21] Appl. No.: 5,877

[22] Filed: Jan. 23, 1979

[30] Foreign Application Priority Data

Jan. 25, 1978 [SE] Sweden .............................. 7800902

[51] Int. Cl.$^2$ ............................................ A61K 35/14
[52] U.S. Cl. .................................................. 424/101
[58] Field of Search ..................................... 424/101

[56] References Cited

U.S. PATENT DOCUMENTS 3,920,625  11/1975  Andersson et al. ............... 424/101

Primary Examiner—Frederick E. Waddell
Attorney, Agent, or Firm—Cushman, Darby & Cushman

[57] ABSTRACT

Concentrates of one of the coagulation factors II, V and VIII or a mixture thereof or blood plasma free from one or more of the coagulation factors VII, IX, X, XI and XII can be prepared by adding a reducing substance comprised of dithiothreitol, dithioerythritol, lipoic acid, mercaptoethanol, or a borohydride to blood or plasma, dithiothreitol being preferred. The amount of reducing substance and the period of time for interaction are so adapted to obtain the product desired, whereafter the blood and plasma, respectively, are optionally fractionated in a known manner.

10 Claims, 1 Drawing Figure

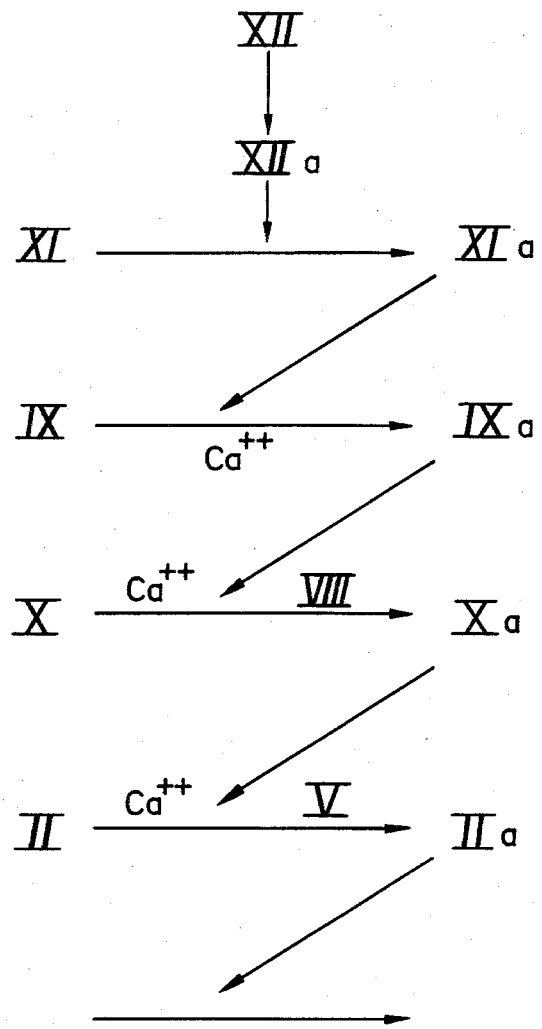

PREPARATION OF BLOOD FRACTION

This invention relates to a process for the preparation of concentrates of one or more of the blood coagulation factors II, V and VIII or plasma free from one or more of the factors VII, IX, X, XI and XII.

Coagulation of blood is a biological amplifying process making it possible that relatively few molecules of initiator product will be required for achieving activation in sequence of a whole series of proteins (proenzymes) circulating in the blood, by proteolysis, which finally leads to a rapid formation of fibrin forming thrombin, e.g. an enzyme cascade which is analogous to a photomultiplying cascade.

BRIEF DESCRIPTION OF THE DRAWING

Blood cogulation is described more in detail with reference to the appended drawing, in which a scheme of the activation of the coagulation factors is shown.

DETAILED DESCRIPTION OF THE DRAWING

These proenzymes in the blood are called coagulation factors and are numbered with Roman figures. With reference to the drawing, in which it is schematically shown how one factor activates the next factor in the so-called intrinsic system, a coagulation process will be described in brief. In the drawing "a" after the number of a factor indicates that the factor is present in activated state. In the so-called extrinsic system the factor VIIa is the activator of factor X together with the tissue thromboplastin.

It is apparent from the drawing that in activation of the factor XII (probably by contact with e.g. collagen) this will be transformed into factor XIIa, which activates factor XI, which will then be transformed into active form (XIa). The factor XIa activates the factor IX (antihemophilic B-factor) and this will then be transormed into the factor IXa in the presence of calcium ions. The factor IXa together with calcium ions, phospholipid and the factor VIII (antihemophilic A-factor) activates the factor X, which is activated to the factor Xa. This factor Xa activates together with calcium ions, phospholipid and the factor V the factor II (prothrombin) to be transformed into its activated form the factor IIa (thrombin), which in its turn causes fibrinogen to be transformed into fibrin.

BACKGROUND OF THE INVENTION

If a coagulation factor is now lacking in the blood the whole reaction sequence is interrupted and formation of fibrin does not occur or takes place only slowly to a small extent. Of the factors of special interest in this respect is the factor VIII, antihemophilic A-factor. An absence of this factor is found in persons with hemophilia (hemophilia A) and such suffering from Willebrand' disease. A lack of the factor VIII can also be considered as acquired.

Due to the great importance of the coagulation factor VIII attempts have been made for a long time to prepare it in more or less concentrated form. By fractionating blood plasma according to Cohn's fractionating method fraction I has been recovered, in which most of the activity of the starting plasma of the factor VIII is found. This fraction I consists for the most part of fibrinogen, but also other proteins (coagulation factors) are found in it. Additional purification takes place by extraction with 1 M glycine solution containing citrate and ethanol (according to Blombäck and Blombäck). The resulting fraction (fraction I-O) has been used in Sweden since 1956 for treatment of hemophilia A.

Preparations with activity of factor VIII have also been obtained from so-called cryoprecipitates, i.e. from precipitates formed in slow thawing at +4° C. of fresh frozen plasma. This cryoprecipitate can be solubilized at 37° C. Preparations with activity of factor VIII have also been prepared by ethanol and polyethylene glycol fractionation. The plasma has then been precipitated in cold with 3% ethanol. Impurities have been adsorbed on aluminium hydroxide, after which polyethylene glycol has been added making it possible to remove fibrinogen from the preparation of factor VIII.

Glycine precipitation has also been used, cryoprecipitate treated with polyethylene glycol being the starting material. It has also been tried to use agarose gel filtrations.

All these known preparation processes have the disadvantage that it is difficult to reproduce them and that they give low yields.

DETAILED DESCRIPTION OF THE INVENTION

Now it has been found that concentrates of one or more of the coagulation factors II, V and VIII or plasma free from one or more of the coagulation factors VII, IX, X, XI and XII can be prepared by adding a reducing agent to blood or plasma, the reducing agent comprising dithiothreitol (DTT), dithioerythritol (DTE), lipoic acid, mercaptoethanol, a borohydride, the amount of reducing agent and the reaction time (incubation time) being adapted according to the desired product, after which the blood and the plasma, respectively, optionally is fractionated in a way known per se. The selection of both amount and time is easily made by one skilled in the art. The fractionation can be made according to Cohn, but also other known methods are useful, as e.g. ammoniumsulfate precipitation, the ether method, the rivanol (2-ethyl-6,9-diaminoacridine lactate) method, precipitation with high polymeric substances and chromatographic methods, as e.g. gel filtration, ion exchange chromatography or affinity chromatography. Dithiothreitol is the most preferred reducing agent; preferred reducing agents are dithioerythritol and lipoic acid. A borohydride, as e.g. an alkaline earth metal or preferably an alkaline metal borohydride, such as potassium or sodium borohydride, is the least preferred reducing agent. In a preferred embodiment the reducing agent is added to blood, which preferably contains an anti-coagulating agent, such as trisodium citrate or directly to plasma. The blood is centrifuged and the resulting plasma is treated according to Cohn for precipitation of fraction I, i.e. is cooled and an ethanol-buffer mixture is added, pH being maintained at 7.0–7.4, preferably about 7.2. The resulting precipitation is separated by centrifugation and the supernatant liquid is in principle further treated according to Cohn for precipitation of fraction II+III. This is made by adding ethanol to the cooled supernatant liquid under cooling and at a pH of 6.8–7.2, preferably 7.0. After centrifuging the supernatant liquid from the precipitation, the precipitation is washed with a diluted aqueous solution of alcohol, usually ethanol, with such a concentration (25% in 0.09 M NaCl) that the precipitation is not dissolved. After washing the precipitation (fraction II+III) is dissolved in a cooled physiological salt solution and is immediately frozen. The present invention will now be described with reference to the following examples:

EXAMPLES OF THE INVENTION

EXAMPLE 1

Human blood with an anti-coagulating agent is centrifuged. 94 mg of reducing agent (DTT, as an aqueous solution, 20 mg/ml) are added to 235 ml plasma. Incubation: 5 min., 37° C., after which iodoacetic acid in aqueous solution is added, 3 mol iodoacetic acid/mol DTT. Then Cohn's fractionation follows:

Fraction I:

The plasma (235 ml) is cooled to 0° C. 41.6 ml of an ethanol solution of 53.3% is cooled and added by drops for 20 min. The cooling bath is then maintained at −3° C., and the temperature is allowed to go down to −3° C. during addition of alcohol. pH of the suspension: 7.3. Stirring for 60 min. at −3.5° C. Centrifuging: 30 min., acceleration 2100 g=about 20 600 m/s², −3° C. Supernatant liquid: volume 270 ml.

Fraction II+III 260 ml supernatant liquid of fraction I are cooled to −3° C. A mixture of 156.3 ml 53.3% EtOH+0.6 ml 95% EtOH+0.34 ml fraction II+III buffer (1 part 4 N NaAc, 2 parts 10 N HAc; pH 4.0.) was cooled and added dropwise. The suspension with pH 6.7 is left to stand for 45 min. with stirring at −5° C. Centrifuging: 30 min., 2100 g=about 20 600 m/s², −5° C. The supernatant liquid is poured off and the precipitation II+III is washed with 250 ml EtOH of 25% in 0.09 M NaCl for 10 min., stirring with a glass rod. Centrifuging: 30 min., acceleration 1700 g=about 16 700 m/s², −5° C. The washing liquid is poured off and the fraction II+III is dissolved in 40 ml cooled (0° C.) 0.15 M NaCl, is distributed in minor portions and is immediately frozen to −70° C.

The activity of coagulation factor VIII (and the other coagulation factors) is determined in a known manner. About 80-90% of the activity of the original plasma of factor VIII is found in the resulting concentrate.

It has also been found that addition of the reducing substance, especially dithiothreitol, to blood reduces the content of the coagulation factors VII, IX, X, XI and XII to a large extent in the plasma resulting from this blood. Also direct addition of the reducing agent to normal trisodium citrate containing plasma inactivates these coagulation factors. This activity will partly return in oxidation, and therefore it is suitable to block the re-oxidation in the preparation of such plasma, e.g. with iodoacetic acid.

EXAMPLE 2

Human blood with anti-coagulating agent (9 parts blood + 1 part 3.8% trisodium citrate) is centrifuged and the following tests with plasma were carried out:

The plasma is divided into 8 ml portions, which are preheated at 37° C. for 5 min. DTT is added in different concentrations, see table 1 below, and is incubated for 5 min. at 37° C. Then iodoacetic acid, 3 mol per mol DTT, is added, and incubation takes place for 15 min. at 37° C. The plasma samples are distributed in portions of about 0.2 ml and are immediately frozen at −70° C. Testing of different coagulation factors is made in known manner.

TABLE 1

| Plasma Samples | Coagulation factors, % of control | | | | | | | |
|---|---|---|---|---|---|---|---|---|
| | F II | F V | F VII | F VIII | F IX | F X | F XI | F XII |
| A. Control plasma | 100 | 100 | 100 | 100 | 100 | 100 | 100 | 100 |
| B. Control plasma + iodoacetic acid (same ampunt as in F.) | 99 | 95 | 108 | 93 | 82 | 96 | 90 | 106 |
| C. Plasma + 0.1 mg DTT/ml plasma + iodoacetic acid | 101 | 94 | 87 | 107 | 129 | 59 | 47 | 78 |
| D. Plasma + 0.1 mg DTT/ml plasma + iodoacetic acid | 69 | 90 | 21 | 86 | 16 | 6 | 9 | 18 |
| E. Plasma + 0.4 mg DTT/ml plasma + iodoacetic acid | 41 | 85 | 6 | 52 | 8 | 0 | 0 | 0 |
| F. Plasma + 0.6 mg DTT/ml plasma + iodoacetic acid | 33 | 90 | 0 | 27 | 0 | 0 | 0 | 0 |

EXAMPLE 3

Human blood with anti-coagulating agent (9 parts blood + 1 part 3.8% trisodium citrate) is centrifuged and the following tests with plasma were carried out:

The plasma is divided into 8 ml portions, which are preheated at 37° C. for 5 min. DTE is added in different concentrations (see table 2), and is incubated for 5 minutes at 37° C. Then, iodoacetic acid (3 mol per mol DTE) is added and incubation is carried out for 15 minutes at 37° C. The plasma samples are distributed in portions of about 0.2 ml and are immediately frozen at −70° C. Testing of different coagulation factors is made in a manner known per se.

TABLE 2

| Plasma Samples | Coagulation factors, % of control | | | | | | | |
|---|---|---|---|---|---|---|---|---|
| | F II | F V | F VII | F VIII | F IX | F X | F XI | F XII |
| A. Control plasma | 100 | 100 | 100 | 100 | 100 | 100 | 100 | 100 |
| B. Control plasma + iodoacetic acid (same amount as in E.) | 100 | 105 | 90 | 115 | 93 | 87 | 98 | 78 |
| C. Plasma + 0.1 mg | | | | | | | | |

TABLE 2-continued

| Plasma Samples | Coagulation factors, % of control | | | | | | | |
|---|---|---|---|---|---|---|---|---|
| | F II | F V | F VII | F VIII | F IX | F X | F XI | F XII |
| DTE/ml plasma + iodoacetic acid | 90 | 99 | 61 | 108 | 61 | 56 | 66 | 78 |
| D. Plasma + 0.2 mg DTE/ml plasma + iodoacetic acid | 66 | 99 | 30 | 116 | 28 | 11 | 3 | 1 |
| E. Plasma + 0.4 mg DTE/ml plasma + iodoacetic acid | 35 | 90 | 48 | 93 | 19 | 2 | 0 | 0 |

EXAMPLE 4

Human blood with anti-coagulating agent (9 parts blood + 1 part 3.8% trisodium citrate) is centrifuged and the following tests with plasma were carried out:

The plasma is divided into 8 ml portions, which are preheated at 37° C. for 5 minutes. Lipoic acid is added in different concentrations (see table 3), and is incubated for 5 minutes at 37° C. Then, iodoacetic acid (3 mol per mol lipoic acid) is added and incubation is carried out for 15 minutes at 37° C. The plasma samples are distributed in portions of about 0.2 ml and are immediately frozen at −70° C. Testing of different coagulation factors is made in a manner known per se.

TABLE 3

| Plasma Samples | Coagulation factors, % of control | | | | | | | |
|---|---|---|---|---|---|---|---|---|
| | F II | F V | F VII | F VIII | F IX | F X | F XI | F XII |
| A. Control plasma | 100 | 100 | 100 | 100 | 100 | 100 | 100 | 100 |
| B. Control plasma + iodoacetic acid (same amount as in E.) | 100 | 105 | 90 | 115 | 93 | 87 | 98 | 78 |
| C. Plasma + 0.1 mg lipoic acid/ml plasma + iodoacetic acid | 100 | 100 | 252 | 111 | 58 | 40 | 67 | 74 |
| D. Plasma + 0.2 mg lipoic acid/ml plasma + iodoacetic acid | 103 | 91 | 203 | 98 | 52 | 26 | 32 | 78 |
| E. Plasma + 0.4 mg lipoic acid/ml plasma + iodoacetic acid | 103 | 215 | 285 | 111 | 58 | 32 | 39 | 98 |

EXAMPLE 5

Human blood with anti-coagulating agent (9 parts blood + 1 part 3.8% trisodium citrate) is centrifuged and the following tests with plasma were carried out:

The plasma is divided into 8 ml portions, which are preheated at 37° C. for 5 minutes. Mercaptoethanol is added in different concentrations (see table 4), and is incubated for 5 minutes at 37° C. Then, iodoacetic acid (3 mol per mol mercaptoethanol) is added and incubation is carried out for 15 minutes at 37° C. The plasma samples are distributed in portions of about 0.2 ml and are immediately frozen at −70° C. Testing of different coagulation factors is made in a manner known per se.

TABLE 4

| Plasma Samples | Coagulation factors, % of control | | | | | | | |
|---|---|---|---|---|---|---|---|---|
| | F II | F V | F VII | F VIII | F IX | F X | F XI | F XII |
| A. Control plasma | 100 | 100 | 100 | 100 | 100 | 100 | 100 | 100 |
| B. Control plasma + iodoacetic acid (same amount as in D.) | 88 | 67 | 104 | 91 | 80 | 86 | 104 | 84 |
| C. Plasma + 0.2 mg mercaptoethanol + iodoacetic acid | 89 | 61 | 69 | 98 | 33 | 75 | 74 | 102 |
| D. Plasma + 0.4 mg mercaptoethanol + iodoacetic acid | 74 | 84 | 29 | 85 | 35 | 37 | 62 | 121 |

EXAMPLE 6

Human blood with anti-coagulating agent (9 parts blood + 1 part 3.8% trisodium citrate) is centrifuged and the following tests with plasma were carried out:

The plasma is divided into 8 ml portions, which are preheated at 37° C. for 5 minutes. Potassium borohydride is added in different concentrations (see table 5, and is incubated for 5 minutes at 37° C. Then, iodoacetic acid (3 mol per mol potassium borohydride) is added and incubation is carried out for 15 minutes at 37° C. The plasma samples are distributed in portions of about 0.2 ml and are immediately frozen at −70° C. Testing of different coagulation factors is made in a manner known per se.

TABLE 5

| Plasma Samples | Coagulation factors, % of control | | | | | | | |
|---|---|---|---|---|---|---|---|---|
| | F II | F V | F VII | F VIII | F IX | F X | F XI | F XII |
| A. Control Plasma | 100 | 100 | 100 | 100 | 100 | 100 | 100 | 100 |
| B. Control plasma + iodoacetic acid (same amount as in D.) | 88 | 67 | 104 | 91 | 80 | 86 | 104 | 84 |
| C. Plasma + 0.14 mg KBH$_4$ + iodoacetic acid | 92 | 74 | 131 | 122 | 77 | 86 | 94 | 86 |
| D. Plasma + 0.28 mg KBH$_4$ + iodoacetic acid | 96 | 93 | 127 | 105 | 71 | 68 | 107 | 83 |

It is also possible to fractionate plasma, which is depleted of the factors VII, IX, X, XI and XII. This fractionation can be carried out according to Cohn for the precipitation of fraction II+III, as described. Then, this fraction II+III contains the factors II, V and VIII. A definite amount of activated factor XI (XIa) obtained by reaction with surface activated factor XII in a way known per se is added to this fraction. Phospholipids, such as inosithine lipid, are also added. After this all is freezedried together with a buffer agent in such amounts that a solution with an optimum pH and an optimum ionic strength is obtained when reforming the agent by means of water.

This agent is especially suitable for determination of the activity of the factors X and IX in the intrinsic coagulation system and for determination of factor VII and X in systems where tissue thromboplastin is added as a cofactor, "the extrinsic coagulation system". Such agents have been difficultly available as previously it has been necessary to have access to plasma from human beings with a great lack of these factors. Such people are rare.

The factors VII, IX and X are proenzymes in blood, which can be activated in different ways (one way is shown in the enclosed drawing). The activated factor X, the factor Xa, acts as prothrombin activator in the coagulation process. Congenital lack of the factors VII, IX and X is rather rare, but the content of these factors will decrease in patients with certain liver diseases and at treatment of patients with dicumarol added at thrombosis diseases.

It is of a very great importance, in the course of treating patients with dicumarol to establish the activity of the vitamin K depending factors with a short half-life, viz. the factors VII, X and IX, as their activity decreases noticeably during this treatment. So far agents have only been available which more or less analyze the sum of all vitamin K depending factors; the same also applies for factor II. The agent obtained in the way described substantially satisfies the requirement of analyzing the sum effect of either the factors X and VII or IX and X depending on which activator is used.

EXAMPLE 7

By addition of reducing agent, e.g. 0.2 mg DTT per ml plasma, at a low temperature, e.g. 22° C., it is possible to selectively influence the decrease of the coagulation activity in the different factors. In example 7 the activity of factor IX is not influenced in as high a degree as the activity of factor X. Such an agent will be valuable in a specific determination of factor X in the so-called intrinsic coagulation system.

What we claim is:

1. A process for the preparation of a blood component selected from the group consisting of a concentrate of at least one of the coagulation factors II, V and VIII and mixtures thereof and plasma free from one of the factors VII, IX, X, XI and XII and mixtures thereof, said process comprising:
    (1) adding a reducing agent selected from the group consisting of dithiothreitol, dithioerythritol, lipoic acid, mercaptoethanol and borohydrides to blood or plasma, the reducing agent added in an amount and for a reaction time sufficient to isolate the desired blood component, and
    (2) fractionating the blood and plasma, respectively, to isolate said blood component.

2. The process of claim 1, wherein the fractionation is made according to Cohn.

3. The process of claim 2, wherein the blood is centrifuged, the resulting plasma is cooled, and ethanol-buffer mixture is added at pH 7.0-7.4 ethanol is added to the cooled supernatant liquid at a pH of 6.8-7.2, the resulting precipitation is washed after separation from the supernatant liquid with an aqueous alcohol and is dissolved in a physiological salt solution for immediate use or freezing.

4. The process of claim 3, wherein said ethanol-buffer mixture is added at a pH of about 7.2.

5. The process of claim 3, wherein said cooled supernatant liquid is at a pH of about 7.0.

6. The process of claim 5, wherein said ethanol-buffer mixture is added under cooling conditions.

7. The process of claim 3, wherein said resulting precipitation is washed after separation from the supernatant liquid with an aqueous solution of ethanol.

8. The process of claim 3, wherein the resulting washed precipitation is dissolved in said physiological salt solution under cooling conditions.

9. The process of claim 1, wherein the antioxidant of claim 1 is iodoacetic acid.

10. The process of claim 1, wherein an antioxidant to prevent re-oxidation is added to the thus isolated blood component of step (2).

* * * * *